(12) United States Patent
Hegg

(10) Patent No.: US 8,845,234 B2
(45) Date of Patent: Sep. 30, 2014

(54) MICROWAVE GROUND, ROAD, WATER, AND WASTE TREATMENT SYSTEMS

(75) Inventor: Vernon R. Hegg, Isanti, MN (US)

(73) Assignee: Microwave Utilities, Inc., Monticello, MN (US)

( * ) Notice: Subject to any disclaimer, the term of this patent is extended or adjusted under 35 U.S.C. 154(b) by 379 days.

(21) Appl. No.: 12/817,852

(22) Filed: Jun. 17, 2010

(65) Prior Publication Data

US 2010/0322713 A1    Dec. 23, 2010

Related U.S. Application Data

(60) Provisional application No. 61/218,152, filed on Jun. 18, 2009, provisional application No. 61/262,378, filed on Nov. 18, 2009.

(51) Int. Cl.

| *E01C 23/14* | (2006.01) |
|---|---|
| *E01H 5/10* | (2006.01) |
| *A01M 1/22* | (2006.01) |
| *E01C 23/06* | (2006.01) |
| *C02F 1/30* | (2006.01) |
| *A01M 19/00* | (2006.01) |
| *A61L 11/00* | (2006.01) |
| *A61L 2/12* | (2006.01) |

(52) U.S. Cl.
CPC .............. *E01C 23/14* (2013.01); *C02F 2303/04* (2013.01); *A01M 1/226* (2013.01); *E01C 23/065* (2013.01); *A61L 11/00* (2013.01); *A61L 2/12* (2013.01); *C02F 1/302* (2013.01); *C02F 2209/02* (2013.01); *E01H 5/106* (2013.01); *A01M 19/00* (2013.01)

USPC ........ 405/131; 405/128.4; 219/690; 219/738; 219/757; 404/77; 404/79

(58) Field of Classification Search
USPC ..................... 405/131, 128.4; 404/77, 79, 95; 277/646, 650; 219/201, 202, 208, 678, 219/679, 690, 736, 738, 756, 757
See application file for complete search history.

(56) References Cited

U.S. PATENT DOCUMENTS

| 3,263,052 | A | * | 7/1966 | Jeppson et al. ................ 219/700 |
| 3,915,582 | A | * | 10/1975 | Clarke .............................. 404/75 |
| 4,175,885 | A | * | 11/1979 | Jeppson .......................... 404/77 |
| 4,252,459 | A | | 2/1981 | Jeppson |
| 4,252,487 | A | | 2/1981 | Jeppson |
| 4,319,856 | A | | 3/1982 | Jeppson |

(Continued)

FOREIGN PATENT DOCUMENTS

| JP | 08-120617 | 5/1996 |
| JP | 09-189008 | 7/1997 |

OTHER PUBLICATIONS

Microdry—Industrial Microwave Technology, http://www.microdry.com/generators.htm, 3 pages, Mar. 23, 2009.

(Continued)

*Primary Examiner* — Tara M. Pinnock
(74) *Attorney, Agent, or Firm* — Patterson Thuente Pedersen, P.A.

(57) ABSTRACT

A microwave ground or road surface heating system that eliminates the need for preparation of the surface to be heated while preventing leakage of microwave radiation. The highly portable microwave heating system prevents leakage of microwave radiation via a microwave horn and sealing shroud configuration that seals the unit to the surface being heated.

17 Claims, 6 Drawing Sheets

(56) References Cited

U.S. PATENT DOCUMENTS

| | | | |
|---|---|---|---|
| 4,347,016 A | 8/1982 | Sindelar et al. | |
| 4,453,856 A * | 6/1984 | Chiostri et al. | 404/91 |
| 4,571,473 A | 2/1986 | Wyslouzil et al. | |
| 4,571,860 A * | 2/1986 | Long | 37/197 |
| 4,590,348 A * | 5/1986 | Lahti et al. | 219/697 |
| 4,619,550 A * | 10/1986 | Jeppson | 404/80 |
| 4,765,773 A * | 8/1988 | Hopkins | 404/94 |
| 5,092,706 A | 3/1992 | Bowen et al. | |
| 5,141,059 A * | 8/1992 | Marsh | 172/1 |
| 5,209,604 A * | 5/1993 | Chou | 405/128.4 |
| 5,245,149 A * | 9/1993 | Pinna et al. | 219/700 |
| 5,370,477 A * | 12/1994 | Bunin et al. | 405/128.65 |
| 5,797,194 A | 8/1998 | Zettergren | |
| 5,829,519 A * | 11/1998 | Uthe | 166/60 |
| 5,895,171 A | 4/1999 | Wiley et al. | |
| 6,127,665 A * | 10/2000 | Tatsumu | 219/754 |
| 6,401,637 B1 | 6/2002 | Haller | |
| 6,554,531 B2 | 4/2003 | Bodish | |
| 7,089,684 B2 | 8/2006 | Genier | |
| 7,413,375 B2 * | 8/2008 | Hall | 404/77 |
| 7,560,673 B2 * | 7/2009 | Wall | 219/700 |
| 7,601,936 B2 * | 10/2009 | Joines | 219/695 |
| 7,607,860 B2 * | 10/2009 | Novak | 404/77 |
| 2002/0090268 A1 | 7/2002 | Haller | |
| 2002/0150425 A1 * | 10/2002 | Bodish | 404/95 |
| 2003/0215354 A1 * | 11/2003 | Clark et al. | 422/22 |
| 2006/0078383 A1 * | 4/2006 | Novak | 404/79 |
| 2006/0198699 A1 | 9/2006 | Hall | |
| 2007/0131603 A1 | 6/2007 | Kantor et al. | |
| 2007/0181496 A1 | 8/2007 | Zuback | |
| 2007/0240975 A1 | 10/2007 | Foret | |
| 2008/0083749 A1 | 4/2008 | Kantor et al. | |

OTHER PUBLICATIONS

Innovation Gallery, http://coe.hkpc.org/html/eng/centres_of_excellence/inno_gallery/zoning/environmental/micro_wav_pur.jsp, 2 pages, Mar. 23, 2009.

PCT Search Report and Written Opinion dated Dec. 29, 2010, Korean Intellectual Property Office, 8 pages.

* cited by examiner

MICROWAVE GROUND, ROAD, WATER, AND WASTE TREATMENT SYSTEMS

PRIORITY CLAIM

The present application claims priority to U.S. Provisional Application Ser. No. 61/218,152, filed Jun. 18, 2009 and entitled "MICROWAVE GROUND, ROAD, WATER, AND WASTE TREATMENT SYSTEMS" and U.S. Provisional Application Ser. No. 61/262,378, filed Nov. 18, 2009 and entitled "MICROWAVE GROUND, ROAD, WATER, AND WASTE TREATMENT SYSTEMS, both of which are herein incorporated by reference in their entirety.

FIELD OF THE INVENTION

The present invention relates to the use of microwaves for heating and treating ground and road surfaces. Other applications include pest control or extermination as well as water, waterwater, and waste treatment via microwave radiation. More particularly, the present invention is directed to a microwave generator in combination with a waveguide, sealing shroud, and control system.

BACKGROUND OF THE DISCLOSURE

There has been and continues to be a very significant need for effective means of thawing frozen ground. Conventional methods used today are slow and antiquated. For example some may use gas or electric energy to directly heat the ground or use gas or electric energy to heat steam or other mediums, which in turn are applied to the frozen ground. Some processes call for drilling holes deep into the frost and injecting steam or gas flames or even inserting small microwave generators in the drilled holes. The most basic systems utilize heated water or other liquids circulated through grids or hoses on the ground surface to thaw the ground. U.S. Pat. No. 5,838,880 to Brooks, et al., incorporated by reference herein in its entirety, describes such a system. These processes are very slow and use an extreme amount of energy.

Previous microwave ground thawing systems were either low frequency 2.45 MHz or very large 915 MHz units with probes placed in predrilled holes to minimize radiation leakage. Predrilling holes for ground thawing took as much or more time and energy then thawing with gas, steam, or other means. An example of a prior microwave ground thawing system is described in U.S. Pat. No. 4,571,473 to Wyslouzil et al., incorporated by reference herein in its entirety.

There continues to be the need for a more efficient ground thawing system that will quickly heat the ground, but addresses the health risks incumbent with microwave radiation.

U.S. Pat. No. 5,092,706 to Bowen, et al, also incorporated by reference herein in its entirety, discloses a microwave system for repairing voids in asphalt pavement, but utilizes a more mobile system for introducing microwave energy to the ground surface. This system suffers from a lack of control in directing the microwave radiation to the ground. This not only results in inefficiency and increased operating costs, but is also unsafe for workers in the area when the system is operational.

Another system that uses microwaves for road repair is disclosed by U.S. patent application Ser. No. 11/306,979 filed by Hall and incorporated by reference herein in its entirety. This system suffers from the fact that it is a large system and fails to address control of the microwave radiation it generates.

Other methods and systems utilizing microwave technology for asphalt road repair include U.S. Pat. Nos. 4,252,459, 4,252,487, and 4,319,856 to Jeppson and 4,347,016 to Sindelar et al., all of which are incorporated by reference herein in their entirety.

SUMMARY OF THE INVENTION

A microwave generation unit of the present invention addresses the deficiencies of prior art ground thawing systems by eliminating the need to prepare the ground by drilling holes for placement of probes that conduct the microwave radiation into the ground. Instead, the microwave generation unit of the present invention comprises a waveguide and sealing shroud that directs microwave energy into the ground from the surface, thus eliminating time-intensive ground preparation. The sealing shroud ensures that microwave radiation leakage is minimized and kept within occupational safety standards.

The present invention provides a system that utilizes microwaves to penetrate into the frozen ground to provide heating and thawing. The microwaves are controlled and monitored using microprocessors and a unique feedback system. Microwave leakage is eliminated by using a liquid filled bladder between the frozen ground and the microwave generator. Microwaves are generated at 915 MHz ranging from 1 to 100 kw and directed through a special waveguide into the frozen ground. Sensors in and around the wave guide monitor the microwave power level, microwave bounce back, ground temperature, and any radiation leakage and the information is fed to a microprocessor.

The invention consists of 915 MHz generator, wave bounce back water load, a wave guide, a wave guide horn, wave guide venting blower, ground sealing bladder, wave leak detectors, wave bounce back sensors, temperature sensors, and microprocessor controller. The complete unit is very portable and can be moved quickly from area to area as it generally takes less than 30 minutes to thaw a nine square foot area.

In another aspect of the present invention, a microwave generation, delivery, and control system is utilized for asphalt road repair. The system described above is used for heating and treating asphalt road surfaces to repair voids (i.e., potholes). The ability to isolate and contain heating of asphalt allows for precision in making repairs. The ability to quickly heat a specific surface also allows for year-round road repair, even in the coldest climates.

In yet another aspect of the present invention, the microwave generation, delivery and control system is utilized for pest control of insects (e.g., red ants) or rodents (e.g., gophers) by safely directing radiation at known areas of infestation to kill the pests. A further aspect of the present invention includes the use of microwave energy to sterilize water, wastewater, and waste materials.

The above summary of the various aspects of the disclosure is not intended to describe each illustrated embodiment or every implementation of the invention. The figures in the detailed description that follow more particularly exemplify these embodiments.

BRIEF DESCRIPTION OF THE FIGURES

The embodiments of the present invention may be more completely understood in consideration of the following detailed description of various embodiments in connection with the accompanying drawings, in which.

Figure 1:
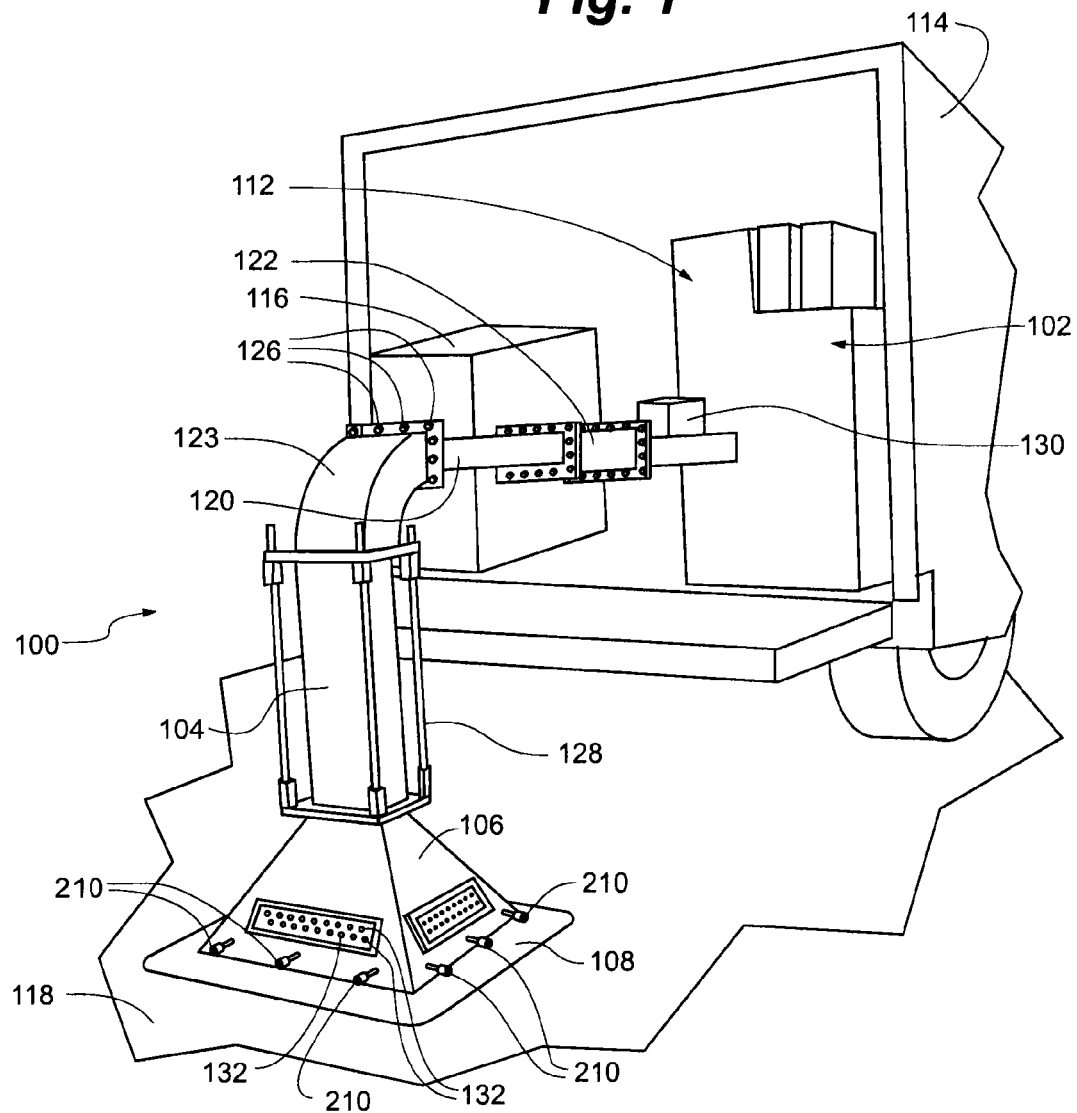
FIG. 1 is a rear perspective of an embodiment of the present invention.
Figure 2:
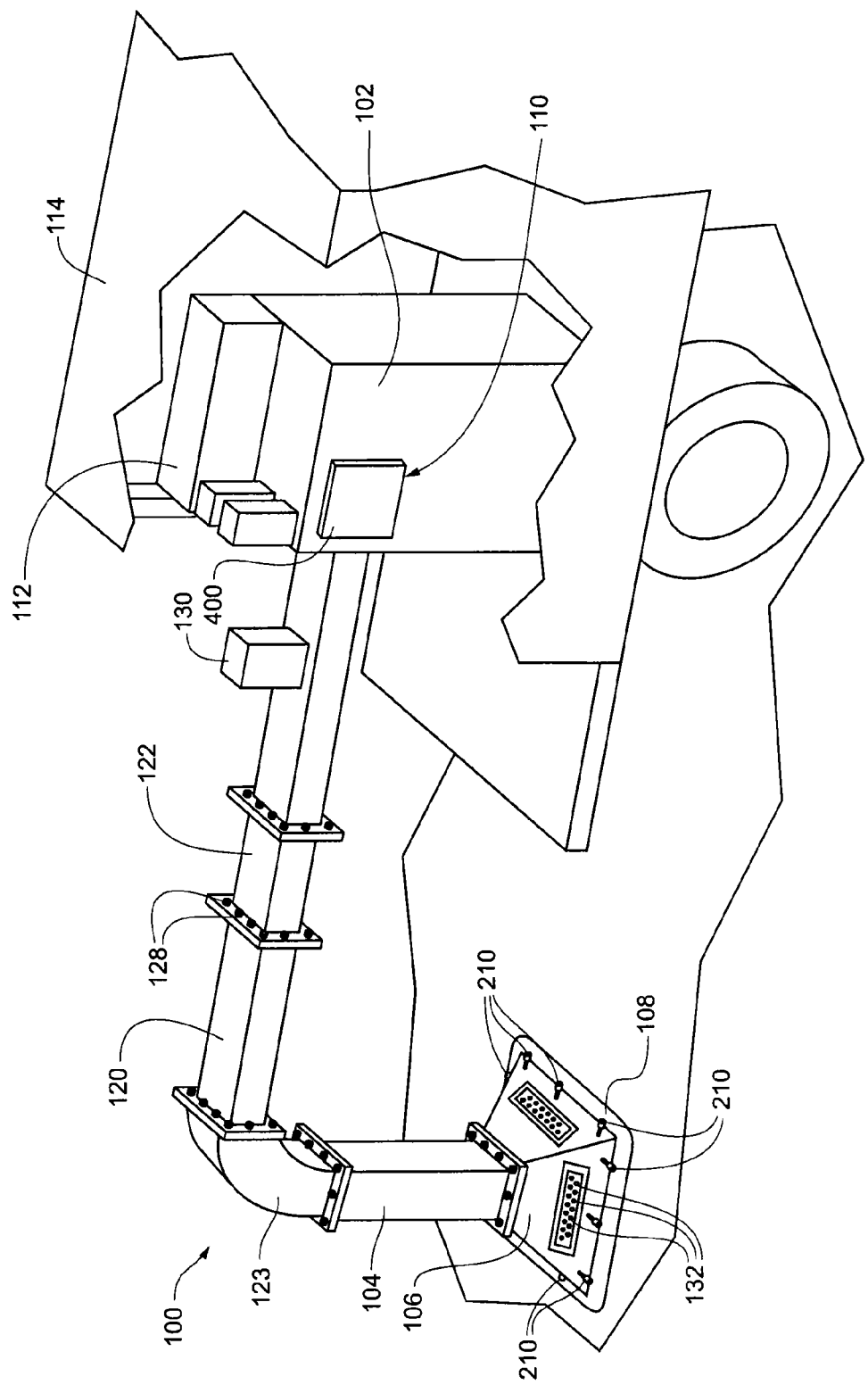
FIG. 2 is a side perspective of an embodiment of the present invention.
Figure 3:
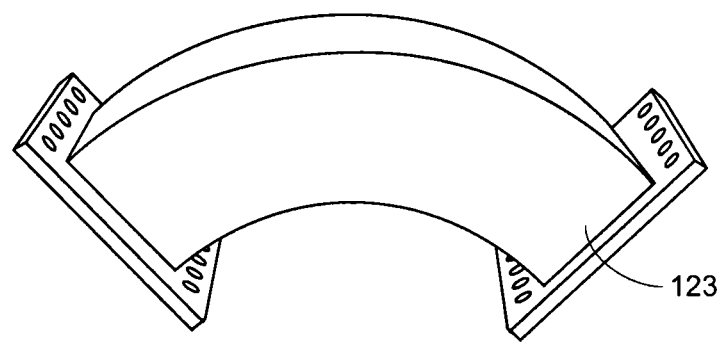
FIG. 3 is a side elevation of a curved portion for the waveguide of the present invention.

While the present invention is amenable to various modifications and alternative forms, specifics thereof have been shown by way of example in the drawings and will be described in detail. It should be understood, however, that the intention is not to limit the present invention to the particular embodiments described. On the contrary, the intention is to cover all modifications, equivalents, and alternatives falling within the spirit and scope of the present invention.

DETAILED DESCRIPTION OF THE FIGURES

Referring now to FIGS. 1-7, a microwave ground heating system 100 of the present invention comprises a microwave generator 102, waveguide 104, horn 106, sealing shroud 108, and control system 110. The microwave generator 102 includes a magnetron 112 capable of producing microwaves preferably at 915 MHz ranging from 1-100 kw. This embodiment allows for mounting on a vehicle 114 for system mobility. The microwave generator 102 will typically require a 3-phase, 460 volt ac power supply 116 that can be mounted on the vehicle 114 or provided from an outside source.

Due to the large quantities of microwave energy used in the present invention, a waveguide 104 will be required to direct the microwave radiation from the microwave generator 102 to the horn 106 for application to the ground or road surface 118. The waveguide 104 consists of non-ferris metals of a thickness of at least ¼ inch. The waveguide 104 of the present invention is preferably comprised of rectangular channels 120, 122 of varying lengths and configurations, such as the curved channel 123 of FIG. 3. The waveguide 104 is not limited to rectangular shape and the present invention contemplates any shape known in the art of microwave energy guidance. To permit articulation of the waveguide 104, one or more rotary joints 124 may be used between channels 120, 122, 123. Rotary joints for waveguides are well known in the art. Examples include U.S. Pat. No. 2,830,276 to Zaleski, U.S. Pat. No. 4,757,281 to Anne et al., and U.S. Pat. No. 3,011,137 to Albanese, all of which are incorporated herein by reference in their entirety. Connections between rectangular channels 120, 122, 123 as well as with rotary joints 124, are preferably made with bolts 126 to allow for relatively easy assembly and disassembly of the waveguide 104. However, it is contemplated that the connections between the various parts of the waveguide 104 can be accomplished by other means such as welding or clamping. For additional stiffness and to provide attachment points for support of the waveguide 104, steel or other stronger metals may be used on the exterior of the waveguide. One embodiment can be a frame 128 as illustrated in FIG. 1. A wave guide venting blower 130 may be used to eliminate any heat or moisture buildup in the waveguide 104.

Figure 4:
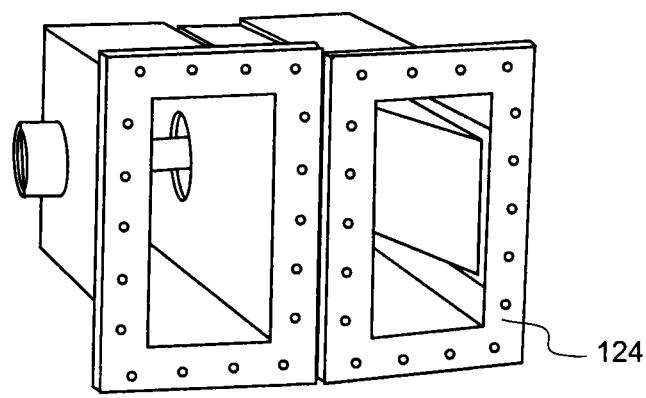
FIG. 4 is a front elevation of a rotary joint for the waveguide of the present invention.

In the presently disclosed embodiment, the waveguide 104 may be moved and placed in a fashion similar to that of a backhoe. For larger or longer waveguides 104, hydraulic systems can be used to move the various parts as with a backhoe boom. Further, the rotary joints 124 of the waveguide 104, as depicted in FIG. 4, will allow the horn 106 to be tilted for non-horizontal application of microwave energy such as to sloped ground.

Figure 5:
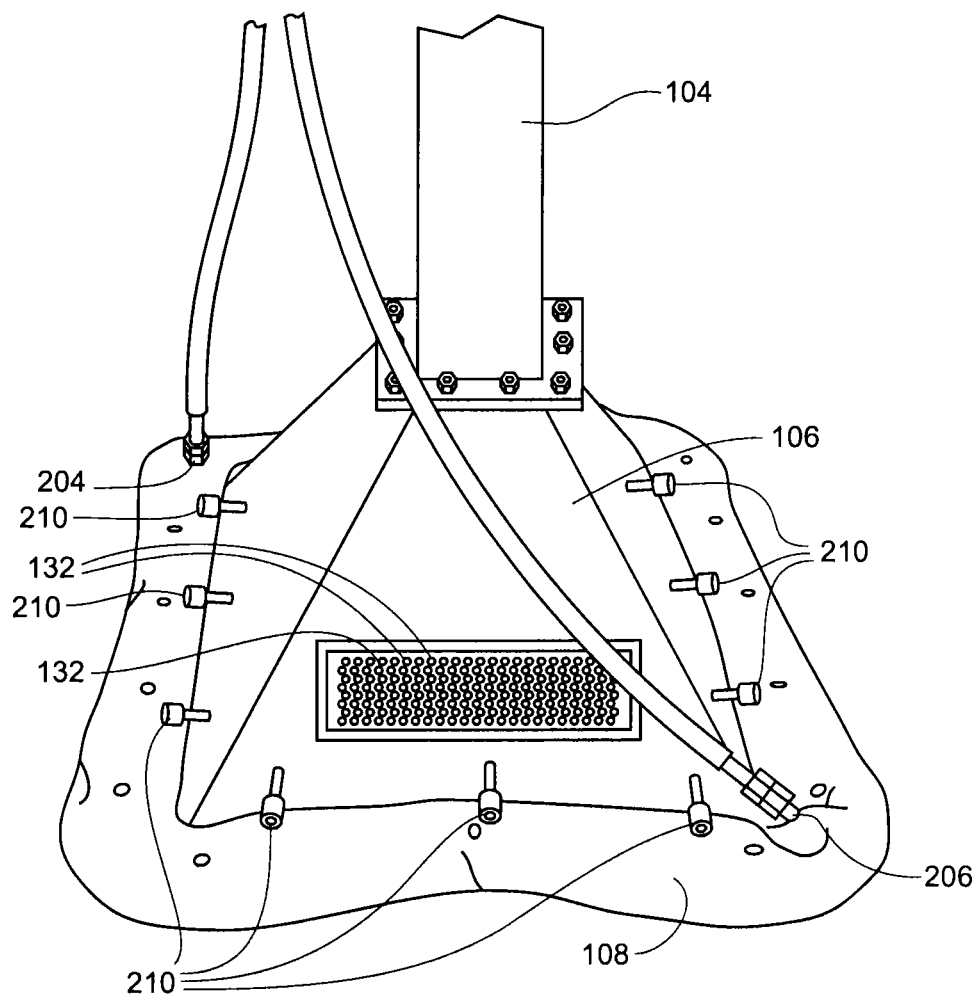
FIG. 5 is a close-up view of the sealing shroud of the present invention.
Figure 6:
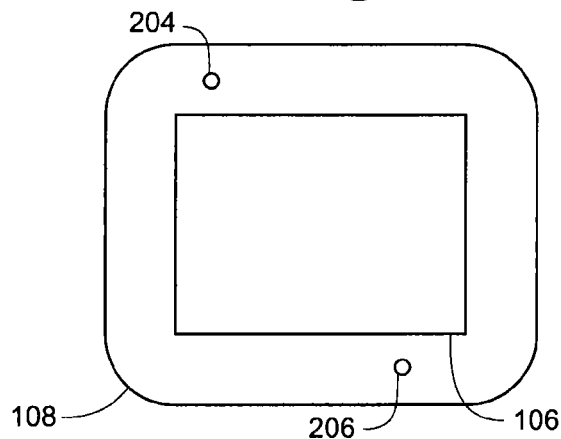
FIG. 6 is a plan view of the sealing shroud of the present invention.
Figure 7:
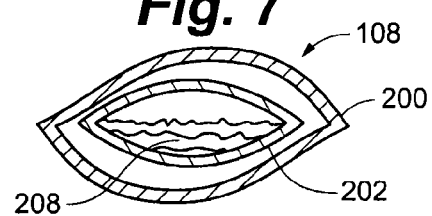
FIG. 7 is a cross-sectional view of the bladder portion of the sealing shroud of FIG. 6.

In the presently contemplated embodiment, the waveguide 104 directs microwave energy through the horn 106 for application to the ground or road surface 118. The horn includes several ventilation ports 132 to allow steam produced during the heating of the ground or road surface 118 to dissipate. To provide a close-fit of the horn 106 to the ground or road surface 118 and limit microwave radiation leakage, a sealing shroud 108 is fitted to the bottom edge of the horn 106 as shown in FIG. 5. The sealing shroud 108 is comprised of a canvas cover 200 for durability and an inflatable rubber bladder 202. For a horn 106 with a footprint of approximately 30 inches by 30 inches, the canvas cover 200 is preferably ⅜ inch in thickness and the rubber bladder 202 is preferably ⅛" in thickness. The horn can be sized for various applications, from a post hole sized horn to a 6-foot by 4-foot sized horn for trenches. The sealing shroud 108 will vary in size and construction accordingly. The sealing shroud 108 also includes inlet and outlet ports 204, 206 for circulation of coolant 208. Coolant 208 is preferably a 50-50 mixture of water and glycol, but can be any form of coolant known to those skilled in the art of liquid cooling. The horn 106 includes several RF sensors 210 located preferably in close proximity to the sealing shroud 108 and spaced around the horn 106 to monitor leakage of microwave radiation.

Figure 8:
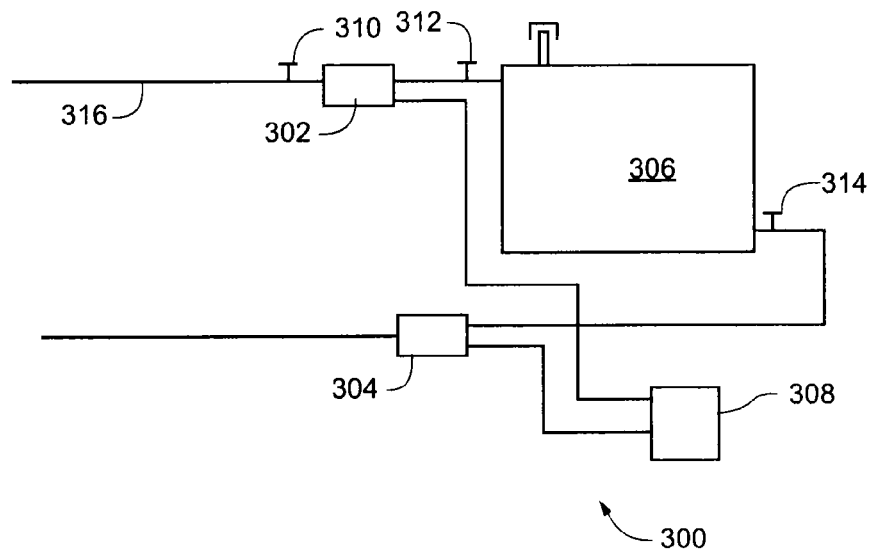
FIG. 8 is a schematic of the cooling system of the present invention.

A liquid cooling system 300 as illustrated in FIG. 8 is provided to cool the sealing shroud 108 during operation of the microwave ground heating system 100. The liquid cooling system 300 comprises an inlet pump 302, an outlet pump 304, a coolant storage tank 306, a temperature monitor 308, and a pressure regulator 310 to circulate the coolant through the sealing shroud 108. Preferably, the inlet and outlet pumps 302, 304 run on 110 volt ac and capable of pumping 30 gallons per minute at 30 psi. In the preferred embodiment of microwave ground heating system 100 with a horn 106 that is 30 inches by 30 inches in footprint, a ½ inch coolant line 316 circulates coolant 208 at a rate of 3-7 gallons per minute at a pressure of 1-3 psi. The system is controlled by a pressure regulator 308, temperature monitor 310, and valves 312, 314 by the control system 110. For this configuration, the coolant storage tank 306 should have a volume of at least 15 gallons.

The present invention also includes a control system 110 with a microprocessor 400 to monitor and control the operation of the microwave generator 102. The control system 110 is programmed to allow inputs such as type of surface to be heated (e.g., clay, sand, asphalt), types of buried utilities, and time to thaw, which will then allow control system 110 to regulate and monitor the operation of the microwave generation unit 102. The control system 110 includes temperature sensors (not shown) and microwave bounce back sensors (not shown) to collect data for control and operation of the microwave generator 102. The control system 110 also receives feedback from the several RF sensors 210 to moderate the microwave energy produced and, if necessary, completely shut down the microwave generation unit 102. The control system 110 also manages the liquid cooling system 300.

In operation, the horn 106 with attached sealing shroud 108 is placed on the ground or road surface 118 to be heated or thawed. Sealing shroud 108 placement is confirmed to ensure that there are no large gaps between it and the ground or road surface 118 that could result in microwave leakage. The control system 110 is then energized and runs a self check to ensure that it has proper communication with other elements of the microwave ground heating system 100. The liquid cooling system 300 is then energized via the control system 110 to circulate coolant 208 prior to energizing the microwave generator 102. As the liquid cooling system 300 pumps coolant 208 into the rubber bladder 202, the sealing shroud 108 expands to fill any gaps between the horn 106 and ground or road surface 118.

The control system 110 then performs a check of all functions of the microwave generation unit 102. This entails warming up the microwave generation unit 102 and supplying it with low power, approximately 3.0 kW, to check parameters such as microwave leakage at key junctions: microwave generation unit 102 to waveguide 104; between rectangular channels 120, 122, 123; between rectangular channels 120, 122, 123 and rotary joints 124; between rectangular channels 120, 122, 123 and the horn 106; and between the horn 106 and the ground or road surface 118. If any parameter exceeds specifications, the control system 110 shuts down the microwave generation unit 102 and the control system 110 indicates via visual and or audio signals where the microwave ground heating system 100 exceeds specifications. Corrections can be made by the system operator and the procedure can be started from the beginning.

Figure 9:
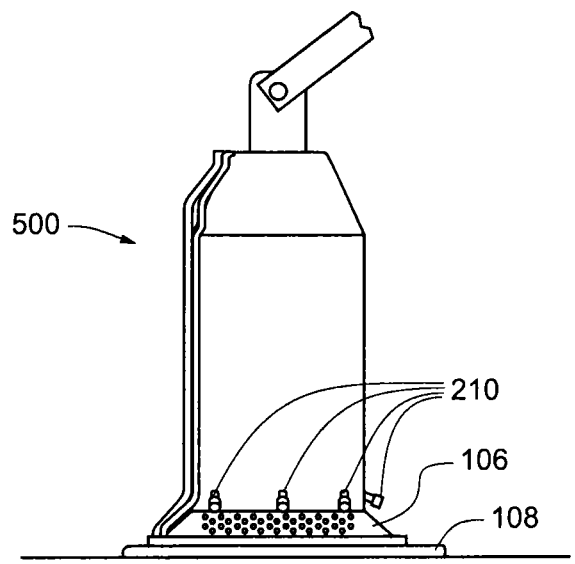
FIG. 9 is a perspective of an alternative embodiment of the present invention.

Another embodiment of the microwave ground heating system 100 is illustrated in FIG. 9. In the alternative embodiment shown in FIG. 9, all of the elements of the microwave ground heating system 100 except for the power supply are provided in a stand-alone unit 500. The stand-alone unit 500 comprises the control system 110, microwave generation unit 102, liquid cooling system 300, horn 106, and sealing shroud 108 of the previously disclosed embodiment. The stand-alone unit 500, eliminates the need for the waveguide 104 of the previously disclosed embodiment. The power supply 116 of the embodiment shown in FIG. 10 can be truck mounted with a boom to assist in placement of the stand-alone unit 500.

Figure 10:
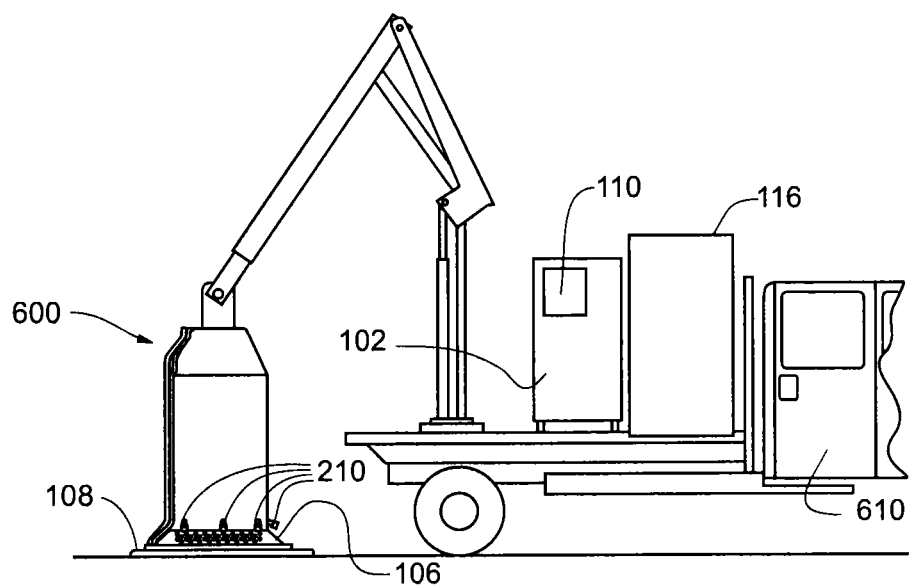
FIG. 10 is a side elevation of a third alternative embodiment of the present invention.

A third embodiment of the microwave ground heating system 100 is illustrated in FIG. 10. In the alternative embodiment shown in FIG. 10, the elements of the microwave ground heating system 100 are provided in a split configuration with some of the elements provided on a base unit 600 and others elements provided on a transport vehicle 610. The base unit 600 comprises at least the horn 106 and sealing shroud 108 of the first disclosed embodiment. The power supply is provided on the transport vehicle 610. The control system 110, microwave generation unit 102, and liquid cooling system 300 of the first disclosed embodiment can be constructed with the base unit 600 or provided on the transport vehicle 610.

OTHER APPLICATIONS

Another application contemplated by the present invention is the use of the microwave ground heating system 100 for road repair. The ability to repair roads, especially asphalt roads, during late fall through winter and early spring is limited in many parts of the world due to cold temperatures. The compacted base cools the asphalt too quickly before it is packed to the optimal air content. Therefore, repair of roads during this time frame is usually limited to repairs with cold-mix asphalt. Such repairs are temporary and will usually require replacement with a hot-mix asphalt when temperatures moderate. Thus, there is a need to provide a portable heating system that can quickly and efficiently heat the area of an asphalt void (i.e., pothole) during cold temperatures that will allow hot-mix asphalt repair.

U.S. Pat. No. 5,092,706 to Bowen, et al, incorporated by reference herein in its entirety, discloses a microwave system for repairing voids in asphalt pavement, but utilizes a more mobile system for introducing microwave energy to the ground surface. This system suffers from a lack of control in directing the microwave radiation to the ground. This not only results in inefficiency and increased operating costs, but is also unsafe for workers in the area when the system is operational.

Another system that uses microwaves for road repair is disclosed by U.S. patent application Ser. No. 11/306,979 filed by Hall and incorporated by reference herein in its entirety. This system suffers from the fact that it is a large system and fails to address control of the microwave radiation it generates. Other methods and systems utilizing microwave technology for asphalt road repair include U.S. Pat. Nos. 4,252,459, 4,252,487, and 4,319,856 to Jeppson and 4,347,016 to Sindelar et al., all of which are incorporated by reference herein in their entirety.

Yet another application contemplated by the present invention is the use of the microwave ground heating system 100 for pest control. Insect and rodent infestations can be problematic to rectify because these pests are typically found below the ground surface. Typical treatment for red ants or gophers is to soak a known area of infestation with poison. This remedy has the shortcomings of potential health risks, especially for young children, and environmental damage. The current invention kills the insects or rodents below grade while leaving no waste products behind.

Other applications of the invention disclosed herein include utilization of microwaves as a disinfectant in the treatment of water and wastewater. In the same vein, it is contemplated that the invention herein described may be used in the treatment of waste materials to disinfect and decontaminate the waste prior to disposal or other dispensation. The material to be treated would be conveyed under the horn of the microwave ground heating system 100 via any of the means known in the art.

It will thus be seen according to the present invention a single use, disposable filtration system for pharmaceutical application and associated methods of use have been disclosed. While the invention has been described in connection with what is presently considered to be the most practical and preferred embodiment, it will be apparent to those of ordinary skill in the art that the invention is not to be limited to the disclosed embodiment, that many modifications and equivalent arrangements may be made thereof within the scope of the invention, which scope is to be accorded the broadest interpretation of the appended claims so as to encompass all equivalent structures and products.

The invention claimed is:

1. A ground surface microwave heating system, comprising:
   a microwave generation system;
   a waveguide; and
   a microwave horn comprising an electrically nonconductive sealing shroud located between the horn and the ground surface, the sealing shroud contacting the ground surface and comprising an inflatable bladder and a durable, flexible cover.

2. The microwave heating system of claim 1, further comprising a cooling system circulating liquid coolant through the inflatable bladder.

3. The microwave heating system of claim 1, wherein the waveguide comprises multiple members that can be joined in various configurations.

4. The microwave heating system of claim 3, wherein the waveguide further comprises a rotary joint.

5. The microwave heating system of claim 3, wherein the waveguide further comprises and external skeleton.

6. The microwave heating system of claim 1, wherein microwave horn comprises an RF sensor.

7. The microwave heating system of claim 6, wherein microwave horn further comprises a ventilation port.

8. The microwave heating system of claim 1, further comprising a control system.

9. The microwave heating system of claim 8 wherein the control system comprises a programmable microprocessor that monitors the generation and leakage of microwave radiation from the heating system.

10. The microwave heating system of claim 9 wherein the microwave generation system generates microwaves at 915 Mhz.

11. A ground surface microwave heating system, comprising: a microwave generation system; and
a microwave horn comprising an electrically nonconductive sealing shroud, the sealing shroud located between the horn and the ground surface, the sealing shroud contacting the ground surface, and the sealing shroud comprising an inflatable bladder and a durable, flexible cover.

12. The microwave heating system of claim 11, further comprising a cooling system circulating liquid coolant through the inflatable bladder.

13. The microwave heating system of claim 12, further comprising a control system.

14. The microwave heating system of claim 13 wherein the control system comprises a programmable microprocessor that monitors the generation and leakage of microwave radiation from the heating system; and
the microwave generation system generates microwaves at 915 Mhz.

15. A method of heating a ground surface comprising:
generating microwave radiation at 915 Mhz;
directing said microwave energy to a ground surface via a waveguide and horn;
preventing the leakage of microwave energy between the horn and the ground surface by providing an electrically nonconductive sealing shroud between the horn and the non-paved ground surface, the sealing shroud contacting the ground surface and comprises an inflatable bladder and a durable, flexible cover.

16. The method of claim 15, further comprising: providing a cooling system circulating liquid coolant through the sealing shroud.

17. The method of claim 16, further comprising: providing a control system with a programmable microprocessor to monitor the generation and leakage of microwave radiation from the heating system.

* * * * *